United States Patent
Watanabe (10) Patent No.: US 12,262,876 B2
(45) Date of Patent: Apr. 1, 2025

(54) ENDOSCOPE

(71) Applicant: HOYA CORPORATION, Tokyo (JP)

(72) Inventor: Toshiki Watanabe, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 597 days.

(21) Appl. No.: 17/267,863

(22) PCT Filed: Feb. 27, 2020

(86) PCT No.: PCT/JP2020/008093
§ 371 (c)(1),
(2) Date: Feb. 11, 2021

(87) PCT Pub. No.: WO2020/195518
PCT Pub. Date: Oct. 1, 2020

(65) Prior Publication Data
US 2021/0177249 A1    Jun. 17, 2021

(30) Foreign Application Priority Data

Mar. 27, 2019 (JP) .................................. 2019-061431

(51) Int. Cl.
*A61B 1/00*    (2006.01)
*A61B 1/05*    (2006.01)
*A61B 1/12*    (2006.01)

(52) U.S. Cl.
CPC .......... *A61B 1/125* (2013.01); *A61B 1/00091* (2013.01); *A61B 1/05* (2013.01)

(58) Field of Classification Search
CPC . A61B 1/00091; A61B 1/05; A61B 1/12–128; A61B 2018/0097; G02B 23/24
USPC ...................................................... 600/101
See application file for complete search history.

(56) References Cited

U.S. PATENT DOCUMENTS

| | | | | |
|---|---|---|---|---|
| 4,898,574 A | * | 2/1990 | Uchiyama | ........ A61B 17/32037 606/127 |
| 5,343,855 A | * | 9/1994 | Iida | .......................... A61B 1/12 600/157 |
| 5,630,795 A | | 5/1997 | Kuramoto et al. | |
| 5,871,440 A | * | 2/1999 | Okada | ................ A61B 1/00096 600/176 |

(Continued)

FOREIGN PATENT DOCUMENTS

| JP | H05-95891 A | 4/1993 |
|---|---|---|
| JP | 08-126605 | 5/1996 |

(Continued)

OTHER PUBLICATIONS

Official Communication issued in International Bureau of WIPO Patent Application No. PCT/JP2020/008093, dated Apr. 21, 2020.
Office Action issued in Chinese Counterpart Patent Appl. No. 202080004567.X, dated Mar. 23, 2022.
Japanese Office Action mailed on Jul. 5, 2022, for the corresponding Japanese Patent Application No. 2021-117227.

*Primary Examiner* — Timothy J Neal
*Assistant Examiner* — James Edward Boice
(74) *Attorney, Agent, or Firm* — GREENBLUM & BERNSTEIN, P.L.C.

(57) ABSTRACT

An endoscope having a convex observation optical system at the distal end of an insertion portion is provided with an air supply/water supply nozzle for injecting a cleaning fluid toward the observation optical system. The air supply/water supply nozzle is provided with a plurality of outlets from which the fluid is emitted in directions not intersecting with each other.

7 Claims, 10 Drawing Sheets

(56) References Cited

U.S. PATENT DOCUMENTS

| | | | | |
|---|---|---|---|---|
| 2012/0219924 A1* | 8/2012 | Walsh | ............... | A61B 5/0088 |
| | | | | 433/29 |
| 2012/0226104 A1* | 9/2012 | Ikeda | ................. | A61B 1/126 |
| | | | | 600/129 |
| 2013/0131453 A1* | 5/2013 | Imai | ................. | A61B 1/00091 |
| | | | | 600/156 |
| 2013/0331653 A1* | 12/2013 | Zipfel | ............... | A61B 1/00188 |
| | | | | 359/368 |
| 2016/0367120 A1* | 12/2016 | Dupont | ................ | A61B 1/015 |
| 2019/0090723 A1* | 3/2019 | Tanaka | .............. | A61B 1/00094 |
| 2019/0328215 A1* | 10/2019 | Kolberg | ............... | A61B 1/273 |
| 2020/0221929 A1* | 7/2020 | Harada | ............ | A61B 1/00002 |
| 2020/0345210 A1* | 11/2020 | Harada | ............ | A61B 1/00101 |
| 2020/0375444 A1* | 12/2020 | Coffeen | ............ | A61B 1/00006 |
| 2022/0104696 A1* | 4/2022 | Yan | ....................... | A61B 1/126 |

FOREIGN PATENT DOCUMENTS

| | | | | |
|---|---|---|---|---|
| JP | 10-192225 | | | 7/1998 |
| JP | 2002-085339 | | | 3/2002 |
| JP | 2002085339 | A | * | 3/2002 |
| JP | 2011-206229 | | | 10/2011 |
| JP | 2011206229 | A | * | 10/2011 |
| JP | 2012-115421 | | | 6/2012 |
| JP | 2018-094016 | | | 6/2018 |
| JP | 2018094016 | A | * | 6/2018 |
| WO | 2017/135048 | | | 8/2017 |
| WO | 2019/054608 | A1 | | 3/2019 |

\* cited by examiner

ENDOSCOPE

TECHNICAL FIELD

The present invention relates to an endoscope having a convex observation optical system at the distal end of an insertion portion inserted into a body.

BACKGROUND ART

Conventionally, in an endoscope, an observation optical system for imaging a subject is provided at the distal end of an insertion portion to be inserted into a body. Dirt such as mucus, blood and residue is likely to adhere to the surface of such an observation optical system. As described above, if the observation optical system is dirty or the like, it is difficult to take a clear image of the subject.

On the other hand, Patent Literature 1 discloses an endoscope in which a fluid is spread over the entire convex lens by spraying the fluid from diagonally above toward an inclined surface around the convex lens.

Patent Literature 2 discloses a lens cleaning sheath for an endoscope that cleans the entire lens by using a wall surface surrounding the lens for a lens having a large diameter.

Patent Literature 3 discloses an air supply/water supply nozzle of an endoscope which has a plurality of outlet ports and makes each jet smaller to give the jet momentum.

CITATION LIST

Patent Literature

Patent Literature 1: JP 2012-115421 A
Patent Literature 2: JP 2018-094016 A
Patent Literature 3: JP 2002-85339 A

SUMMARY OF INVENTION

Technical Problem

The Coanda effect is known in which the fluid flowing near the wall surface is attracted to the wall surface by the effect of fluid viscosity. Due to such a Coanda effect, in a convex lens, when a fluid flows along a surface (curved surface), the fluid is concentrated toward the center of the curved surface. The fluid concentrated in this way separates from the curved surface of the convex lens. Therefore, when the cleaning fluid is injected onto the convex lens from one nozzle, the cleaning fluid does not reach the side opposite to the nozzle side where the fluid directly hits, resulting in insufficient cleaning.

However, the above-mentioned endoscope of Patent Literature 1, the lens cleaning sheath for the endoscope of Patent Literature 2, and the air supply/water supply nozzle of the endoscope of Patent Literature 3 have not been devised to solve such a problem, and are not able to solve it.

The invention has been made in view of such circumstances, and an object of the invention is to provide an endoscope in which a cleaning fluid can be distributed to the side opposite to the side of the nozzle injecting the fluid, and sufficient cleaning can be performed in a convex observation optical system.

Solution to Problem

An endoscope according to the invention has a convex observation optical system at a distal end of an insertion portion, and includes a nozzle for injecting a cleaning fluid toward the observation optical system. The nozzle includes a plurality of outlets from which the fluid is emitted in directions not intersecting with each other.

In the invention, the nozzle that injects the cleaning fluid toward the observation optical system has a plurality of outlets each emitting the fluids in directions not intersecting with each other. Therefore, it is possible to suppress the fluids from the outlets from merging after emission and concentrating toward the center of the observation optical system, and it is possible to prevent the fluid from leaving the curved surface of the observation optical system.

Advantageous Effects of Invention

According to the invention, in a convex observation optical system, a cleaning fluid can be distributed to the side opposite to the side of the nozzle injecting the fluid, and sufficient cleaning can be performed.

DESCRIPTION OF EMBODIMENTS

Hereinafter, an endoscope according to embodiments of the invention will be described in detail with reference to the drawings.

First Embodiment

Figure 1:
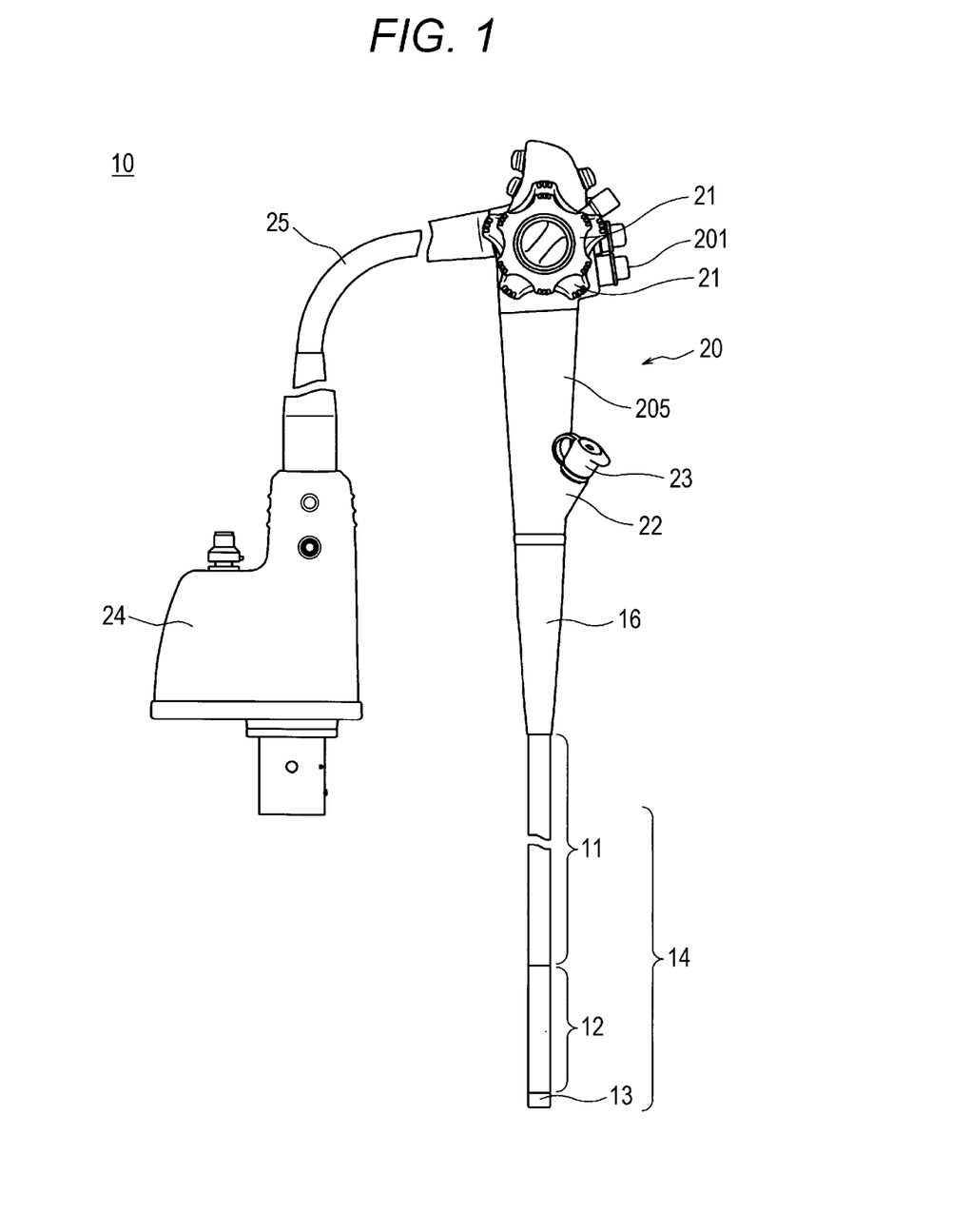
FIG. 1 is an external view of an endoscope according to a first embodiment of the invention.

FIG. 1 is an external view of an endoscope 10 according to the first embodiment of the invention. The endoscope 10 according to this embodiment includes an insertion portion 14, an operation unit 20, a universal cord 25, and a connector portion 24. The operation unit 20 includes a button 201 and a bending knob 21 for receiving a user operation, and a channel inlet 22 provided in a case 205 having a substantially cylindrical shape. A forceps plug 23 having an insertion port for inserting a treatment tool or the like is fixed to the channel inlet 22.

The insertion portion 14 is inserted into the body of a subject. The insertion portion 14 is long and has a distal end portion 13, a bending section 12, and a soft section 11 in this order from one end of the distal end. The other end of the insertion portion 14 is connected to the operation unit 20 via a folding portion 16. The bending section 12 is bent according to an operation of the bending knob 21. The distal end portion 13 is composed of a distal end portion 13a and a distal end portion 13b (see FIG. 9), and the distal end portion 13a is provided on the distal end side of the insertion portion 14 with respect to the distal end portion 13b.

In the following description, a longitudinal direction of the insertion portion 14 is also referred to as an insertion direction. Further, in the insertion direction, the other end side close to the operation unit 20 is referred to as the operation unit side, and the one end side close to the distal end portion 13 is also referred to as the distal end portion side.

The universal cord 25 is long, and has one end connected to the operation unit 20 and the other end connected to the connector portion 24. The universal cord 25 is soft. The connector portion 24 is connected to a processor for an endoscope (not illustrated), a light source device, a display device, an air and water supply device, and the like. By appropriately operating the operation unit 20, the cleaning fluid (air or water) sent through the connector portion 24 is sent to the distal end portion 13 via the folding portion 16.

Figure 2:
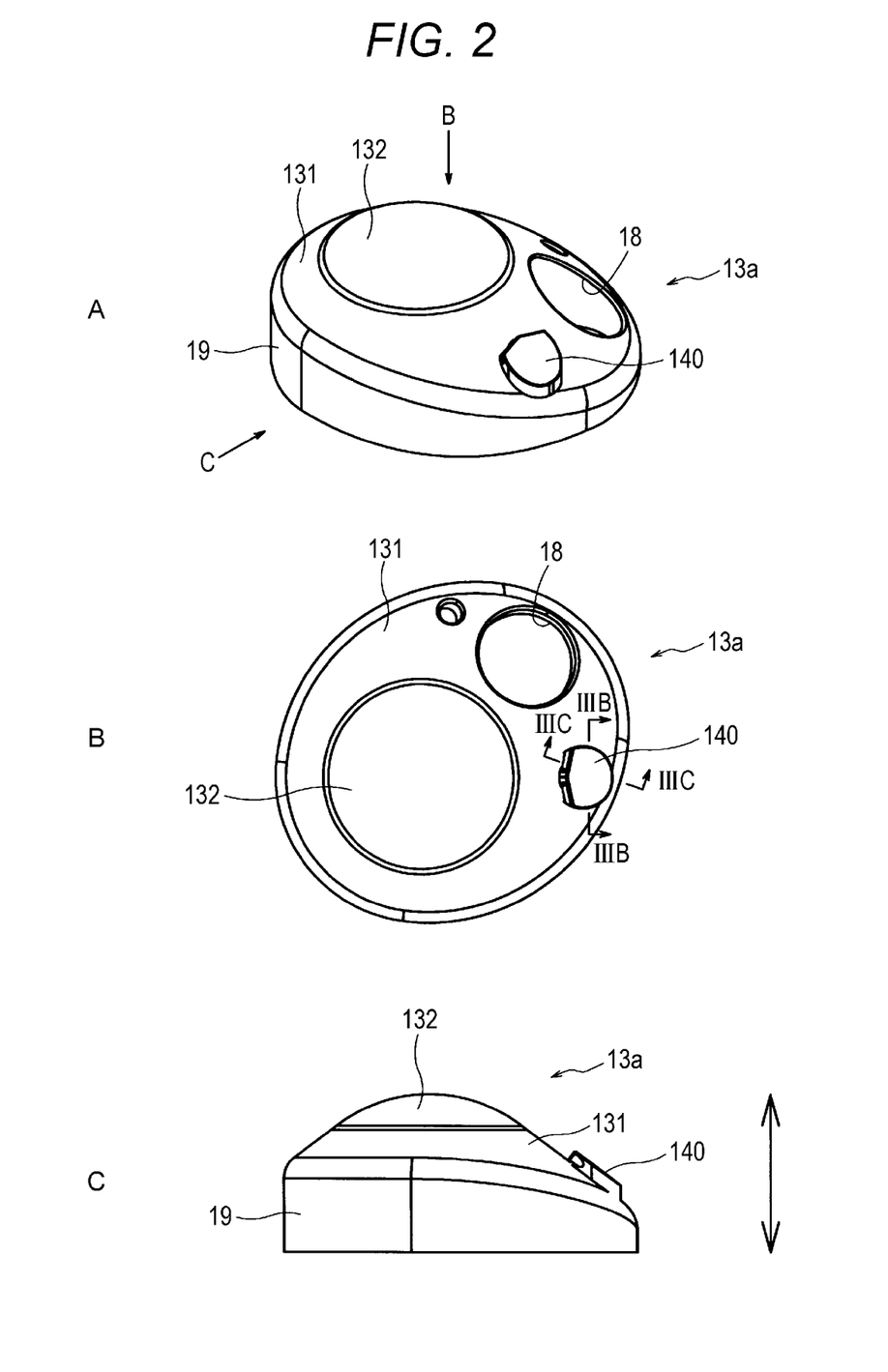
FIG. 2 is an external view of a distal end portion of the endoscope according to the first embodiment of the invention.

FIG. 2 is an external view of the distal end portion 13a of the endoscope 10 according to the first embodiment of the invention. FIG. 2A is a perspective view of the distal end portion 13a. FIG. 2B is a diagram illustrating the distal end portion 13a when viewed from a direction of arrow B of FIG. 2A. FIG. 2C is a diagram illustrating the distal end portion 13a when viewed from a direction of arrow C of FIG. 2A.

The distal end portion 13a is substantially elliptical in cross section, and has the distal end protruding in a substantially conical shape. The distal end surface 131 of the distal end portion 13a is provided with an observation optical system 132, an air supply/water supply nozzle 140, a channel outlet 18, and the like.

Further, the distal end portion 13a has a cylindrical storage cylinder 19 which houses an image sensor (not illustrated) or the like that captures the image light of the subject via the observation optical system 132 and performs imaging. The distal end surface 131 of the distal end portion 13a extends from the edge of the storage cylinder 19. Air and water transmission paths injected through the air supply/water supply nozzle 140 are formed in the storage cylinder 19, the bending section 12, and the soft section 11.

The observation optical system 132 is provided at the central part of the distal end surface 131 of the distal end portion 13a, and is a circular convex lens. Further, in the distal end surface 131 of the distal end portion 13a, the air supply/water supply nozzle 140 and the channel outlet 18 are provided adjacent to each other around the observation optical system 132.

The distal end surface 131 of the distal end portion 13a looks like a truncated cone. That is, the distal end surface 131 is an inclined surface that is inclined in the tangential direction from the edge portion of the observation optical system 132, and the air supply/water supply nozzle 140 and the channel outlet 18 are formed on such an inclined surface.

Figure 3:
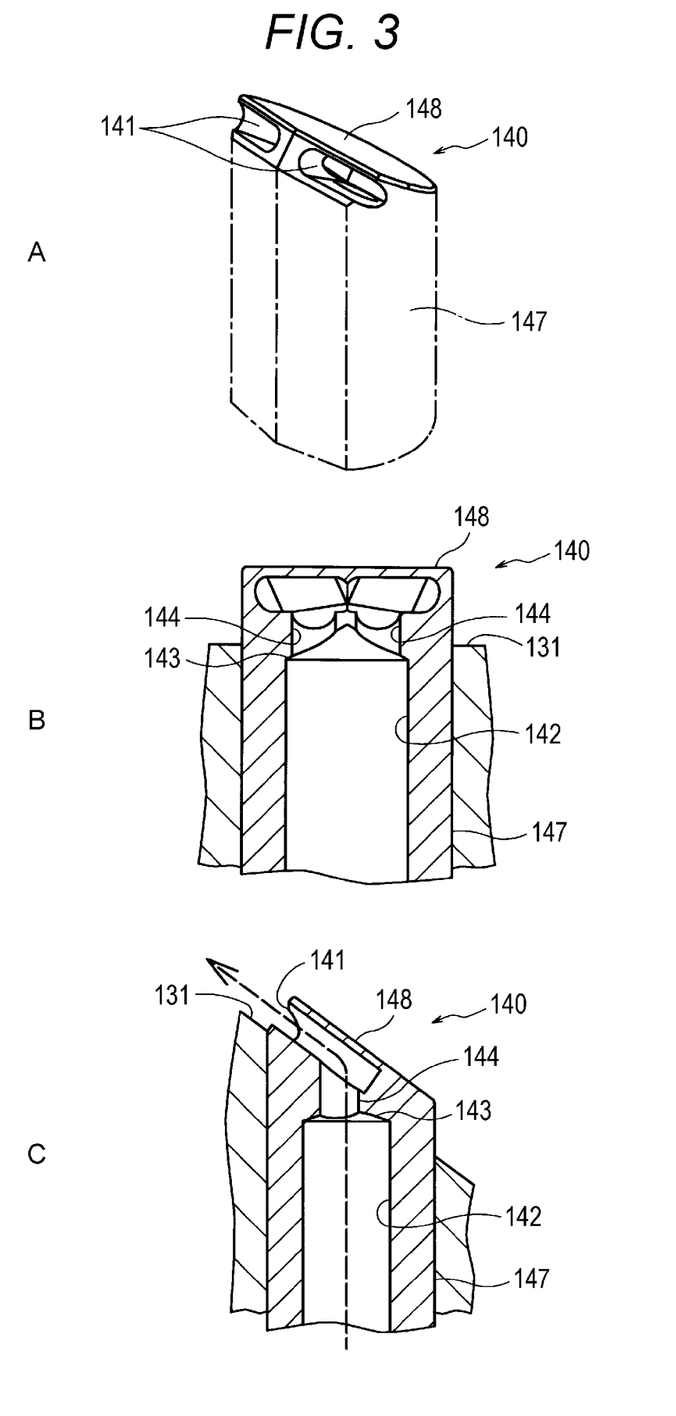
FIG. 3 is a diagram illustrating an air supply/water supply nozzle of the endoscope according to the first embodiment of the invention.

FIG. 3 is a diagram illustrating the air supply/water supply nozzle 140 of the endoscope 10 according to the first embodiment of the invention. FIG. 3A is a perspective view illustrating the appearance of the air supply/water supply nozzle 140, FIG. 3B is a cross-sectional view taken along line MB-111B of FIG. 2B, and FIG. 3C is a cross-sectional view taken along line IIIC-IIIC of FIG. 2B.

The air supply/water supply nozzle 140 injects air or water toward the observation optical system 132 along the distal end surface 131. The air supply/water supply nozzle 140 has a plurality of outlets 141 from which air or water is emitted. Air and water are emitted toward the observation optical system 132 through each outlet 141.

In this embodiment, a case where the air supply/water supply nozzle 140 has two outlets 141 will be described as an example. The invention is not limited to this, and may be configured to have three or more outlets 141.

Each outlet 141 is open in different directions. That is, air or water is emitted through each outlet 141 in a direction that does not intersect with each other. Each outlet 141 has an oval shape with the direction along the distal end surface 131 as the long axis direction. Most part of the air supply/water supply nozzle 140 (the chain line portion in FIG. 3A) is inserted and fixed in a recess provided on the distal end surface 131.

As described above, the observation optical system 132 is provided at the distal end of the distal end portion 13a, and the distal end surface 131 forms a slope so as to surround the circular edge of the observation optical system 132. The air supply/water supply nozzle 140 is provided on the distal end surface 131 separated from the observation optical system 132. That is, in the endoscope 10 according to the first embodiment of the invention, in the longitudinal direction of the insertion portion 14 (see the arrow in FIG. 2C), the air supply/water supply nozzle 140 is arranged at a position closer (the operation unit 20 side) to the other end of the insertion portion 14 rather than the observation optical system 132.

Since the observation optical system 132 is a convex lens and has a wide viewing angle (180 degrees or more), when the air supply/water supply nozzle 140 is arranged at the same position as the observation optical system 132 in the longitudinal direction of the insertion portion 14, the air supply/water supply nozzle 140 appears in the captured image of the observation optical system 132. However, in the endoscope 10 according to the first embodiment of the invention, as described above, the air supply/water supply nozzle 140 is arranged at a position closer to the other end of the insertion portion 14 than the observation optical system 132. Therefore, the air supply/water supply nozzle 140 does not appear in the captured image of the observation optical system 132, and does not interfere with the image capturing by the observation optical system 132.

The air supply/water supply nozzle 140 has a cylinder portion 147 and a lid portion 148 that seals one open end of the cylinder portion 147. The lid portion 148 and the cylinder portion 147 are integrally formed. The lid portion 148 has a substantially disk shape and is inclined with respect to the longitudinal direction of the cylinder portion 147. The air supply/water supply nozzle 140 is provided with the outlet 141 at one end portion on the lid portion 148 side. The air supply/water supply nozzle 140 has a connecting pipe portion 142 extending along the longitudinal direction of the cylinder portion 147 inside the cylinder portion 147. The connecting pipe portion 142 sends air or water sent through the connector portion 24 and the folding portion 16 to each outlet 141. That is, the connecting pipe portion 142 connects an air supply tube 121 and a water supply tube 122 (see FIG. 10) with the outlet 141, and sends air or water flowing into the connecting pipe portion 142 through the opening at one end of the connecting pipe portion 142 toward the outlet 141 on the other end side (the lid portion 148 side).

In the end portion (the end portion on the lid portion 148 side) on the downstream side in the connecting pipe portion 142, there is provided a divergence portion 144 that divides the flow of air or water flowing through the connecting pipe portion 142 corresponding to the number of outlets 141. That is, the downstream side of the connecting pipe portion 142 is divided into two flow paths (the flow divergence portion 144) having a smaller diameter than the connecting pipe portion 142. Each divergence portion 144 is provided so as to correspond to any one of the outlets 141, and the air or water flowing into each divergence portion 144 is emitted through the corresponding outlet 141.

Further, a funnel-shaped or tapered diameter-reduced portion 143 is formed on the downstream side of the connecting pipe portion 142 and on the upstream side of the divergence portion 144. The diameter of the connecting pipe portion 142 on the upstream side of the divergence portion 144 is reduced by the diameter-reduced portion 143. Therefore, the pressure of air or water flowing into each divergence portion 144 through the diameter-reduced portion 143 is reduced, and the flow speed is increased. The air or water having a higher flow speed flows out into a space wider than the divergence portion 144 (see FIGS. 3B and 3C), and flows toward the outlet 141. At this time, air or water forms a vortex having vectors in various directions, and is emitted from the outlet 141. Therefore, the air or water injected from each outlet 141 spreads over a wide range, and can secure an injection force and range at the time of injection. FIG. 3C illustrates the flow path of air or water with a broken line.

As described above, in the air supply/water supply nozzle 140, the directions of the outlets 141 are different from each other, and the air or water from each outlet 141 is emitted in a direction that does not intersect with each other. That is, if air or water is emitted linearly through the outlet 141 and maintains the linearity even after the emission, each outlet 141 is provided such that the air or water from each outlet 141 does not intersect with each other.

With such a configuration, the endoscope 10 according to this embodiment can clearly clean the observation optical system 132 up to the opposite side of the air supply/water supply nozzle 140 side, where the air or water directly hits in the observation optical system 132 which is a convex lens, even using one air supply/water supply nozzle 140. Hereinafter, the portion opposite to the air supply/water supply nozzle 140 side in the observation optical system 132 is referred to as the nozzle opposite side.

In general, the fluid flowing near the wall surface is attracted to the wall surface by the effect of fluid viscosity (called the Coanda effect). Due to such a Coanda effect, when a fluid flows along the surface (curved surface) of a convex lens, the fluid exhibits a behavior of concentrating toward the center of the curved surface. The fluid concentrated in this way separates from the curved surface of the convex lens. Therefore, when air or water (cleaning fluid) is injected to the observation optical system from one air supply/water supply nozzle (outlet), the air or water does not reach the nozzle opposite side in the observation optical system, and the cleaning of the observation optical system becomes insufficient.

Even if the outlet of the air supply/water supply nozzle is widened and air or water is sprayed over a wide range of the observation optical system, the air or water emitted from the outlet is concentrated toward the center of the observation optical system. Therefore, as described above, the separation from the curved surface of the observation optical system occurs.

Further, even when the air supply/water supply nozzle has a plurality of outlets and air or water is injected from the plurality of outlets, the air or water from one outlet starts to spread after the emission, and the air or water from the other outlets merge together. Therefore, as described above, the air or water concentrates toward the center, and are separated from the curved surface of the observation optical system.

On the other hand, in the endoscope 10 according to the first embodiment of the invention, the air supply/water supply nozzle 140 has two outlets 141 having different orientations. Therefore, it is possible to suppress the air or water emitted from one outlet 141 from merging with the air or water emitted from the other outlet 141. Therefore, it is possible to prevent the air or water from concentrating toward the center of the observation optical system 132 and separating from the curved surface of the observation optical system 132 in advance, and the air or water for cleaning can flow to the nozzle opposite side in the observation optical system 132.

Further, since air or water from each outlet 141 approaches the center of the observation optical system 132 due to the Coanda effect, the entire observation optical system 132 can be sufficiently cleaned including the center portion of the observation optical system 132 where air or water is not directly injected.

Figure 4:
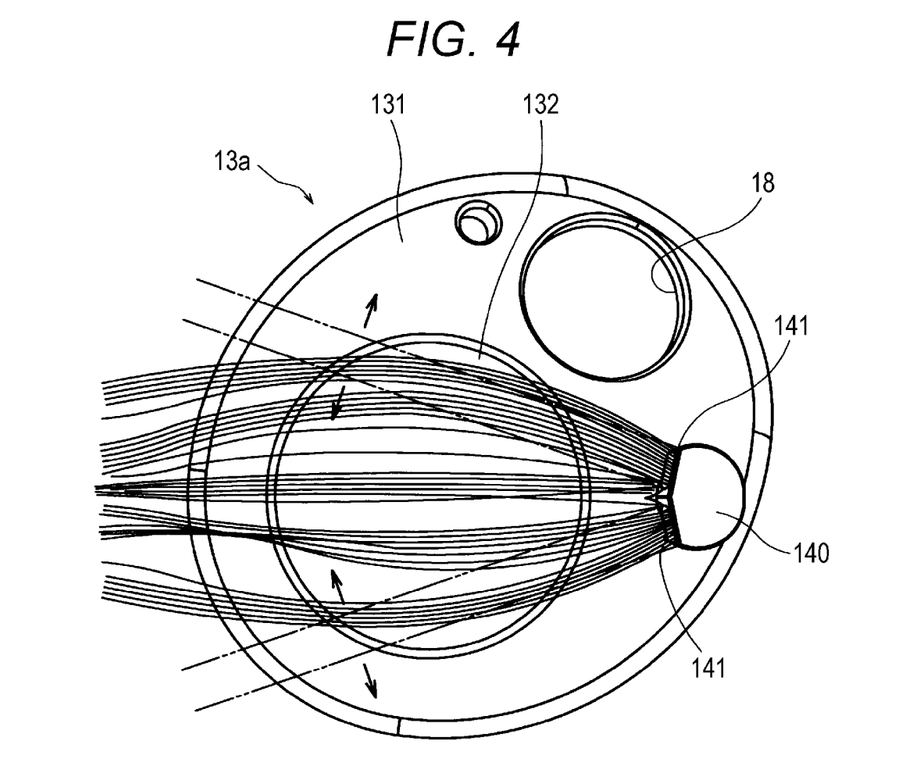
FIG. 4 is a result of simulating the flow path of air or water ejected by the air supply/water supply nozzle in the endoscope according to the first embodiment of the invention.
Figure 5:
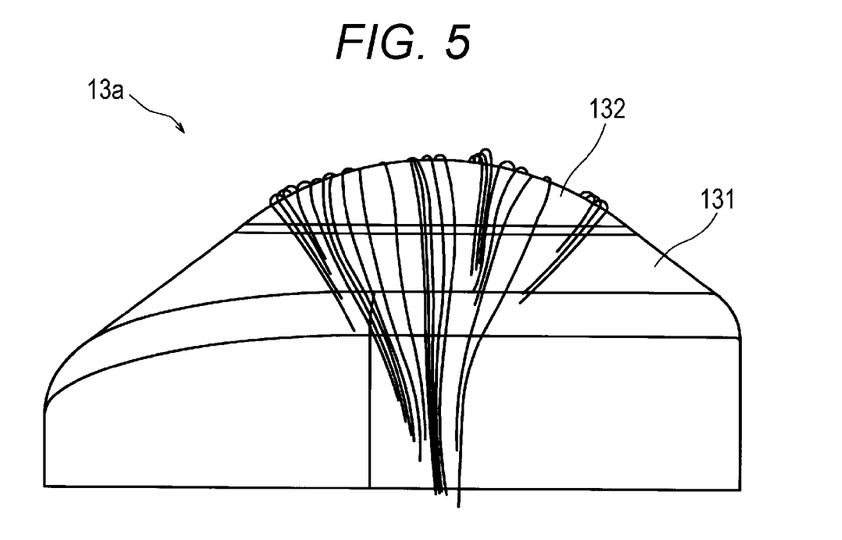
FIG. 5 is a result of simulating the flow path of air or water ejected by the air supply/water supply nozzle in the endoscope according to the first embodiment of the invention.

FIGS. 4 and 5 are the results of simulating the flow path of air or water ejected by the air supply/water supply nozzle 140 in the endoscope 10 according to the first embodiment of the invention. FIG. 4 mainly illustrates the upstream side of the flow path, and FIG. 5 mainly illustrates the downstream side. That is, FIG. 5 illustrates the flow path on the nozzle opposite side in the observation optical system 132. Further, in FIG. 4, the chain line indicates the direction of each outlet 141, and the solid line indicates the flow path of air or water emitted from the outlet 141.

As can be seen from FIGS. 4 and 5, in the endoscope 10 according to the first embodiment of the invention, the air or water emitted from one outlet 141 starts to spread after the emission (see arrow in FIG. 4). However, there is almost no merging with air or water emitted from the other outlet 141, no concentration in the center of the observation optical system 132 is found, and the separation from the curved surface of the observation optical system 132 does not occur. Air or water is flowing to the nozzle opposite side in the observation optical system 132 (see FIG. 5).

In the above description, the case where the distal end surface 131 is inclined with respect to the longitudinal direction of the insertion portion 14 has been described as an example, but the invention is not limited to this.

Figure 6:
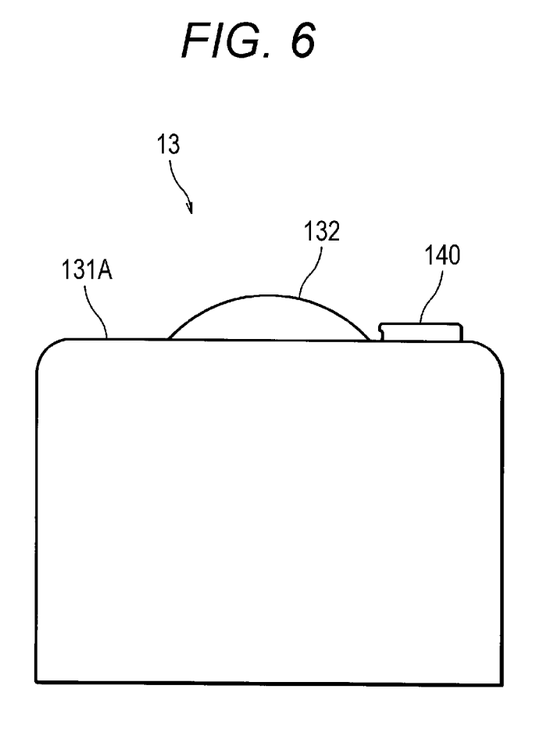
FIG. 6 is an exemplary view illustrating a case where the distal end surface is a flat surface in the endoscope according to the first embodiment of the invention.

FIG. 6 is an exemplary view illustrating the case where a distal end surface 131A is a flat surface in the endoscope 10 according to the first embodiment of the invention. As illustrated in FIG. 6, even in a case where the distal end surface 131A is a flat surface, it is a matter of course that the above-mentioned effect is obtained.

Second Embodiment

Figure 7:
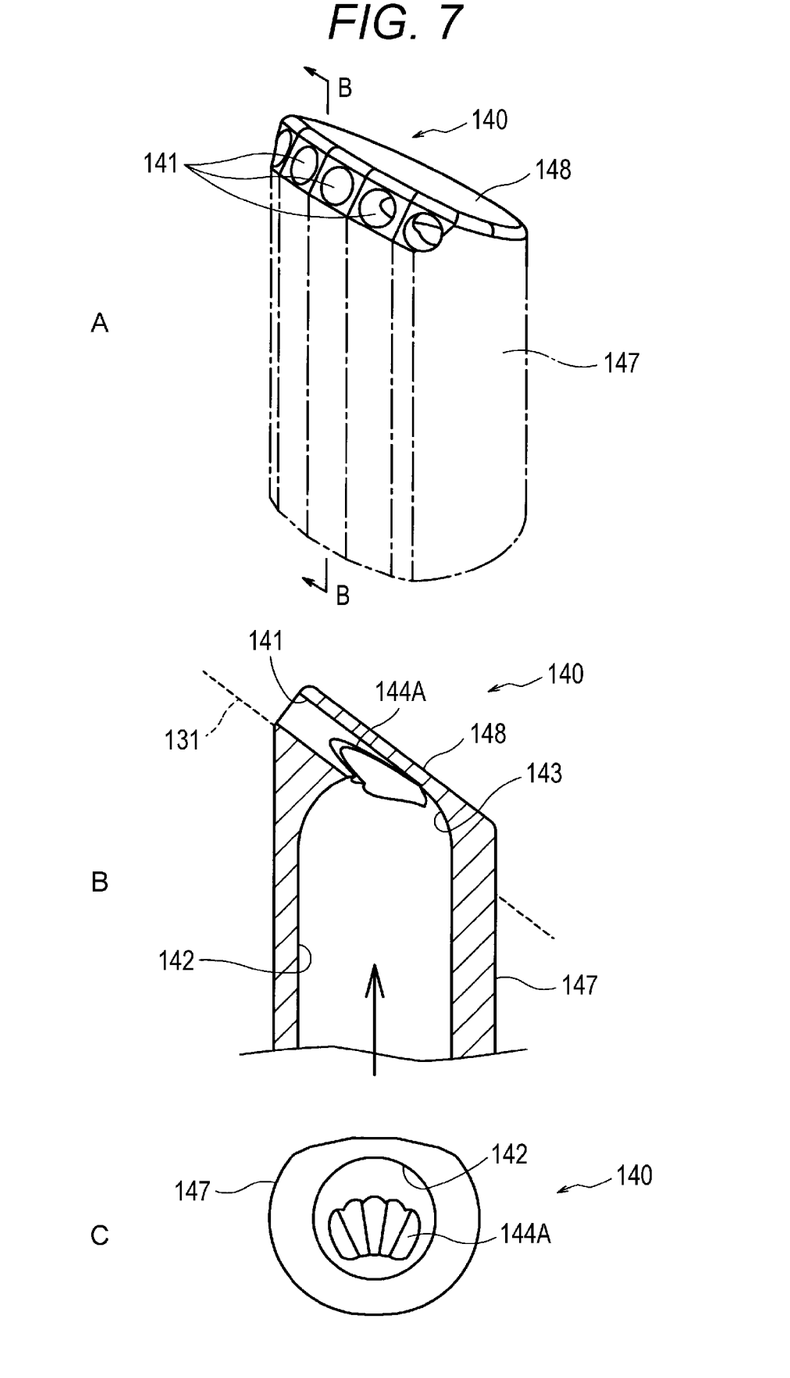
FIG. 7 is a diagram illustrating an air supply/water supply nozzle of an endoscope according to a second embodiment of the invention.

FIG. 7 is a diagram illustrating an air supply/water supply nozzle 140 of the endoscope 10 according to the second embodiment of the invention. FIG. 7A is a perspective view illustrating the appearance of the air supply/water supply nozzle 140, FIG. 7B is a cross-sectional view taken along line B-B of FIG. 7A, and FIG. 7C is a diagram seen from the arrow direction of FIG. 7B. In FIG. 7A, the portion inserted into the recess provided in the distal end surface 131 is indicated by a chain line, and in FIG. 7B, the distal end surface 131 is indicated by a broken line.

The air supply/water supply nozzle 140 according to the second embodiment of the invention has five outlets 141. Each outlet 141 has a circular shape. The five outlets 141 are arranged side by side in a row, and each outlet 141 has a different orientation.

The air supply/water supply nozzle 140 has a cylinder portion 147 and a lid portion 148 that seals one open end of the cylinder portion 147. The lid portion 148 and the cylinder portion 147 are integrally formed. The lid portion 148 has a substantially disk shape and is inclined with respect to the longitudinal direction of the cylinder portion 147. The air supply/water supply nozzle 140 is provided with the outlet 141 at one end portion on the lid portion 148 side. The air supply/water supply nozzle 140 has a connecting pipe portion 142 extending along the longitudinal direction of the cylinder portion 147 inside the cylinder portion 147. The connecting pipe portion 142 sends air or water sent through the connector portion 24 and the folding portion 16 to each outlet 141.

On the downstream side (the lid portion 148 side) of the connecting pipe portion 142, there is provided a divergence portion 144A for dividing the flow of air or water in the connecting pipe portion 142 corresponding to the number of outlets 141. The divergence portion 144A is composed of five recesses provided on the inner surface of the lid portion 148. These five recesses are connected in series, and each recess extends to the outlet 141 side. The bottom of each recess is curved, and the dimension of the bottom is shorter as it goes to the outside. Each recess corresponds to any one of the outlets 141.

Air or water is divided into five flow paths on the downstream side of the connecting pipe portion 142 by the divergence portion 144A. That is, each recess of the flow divergence portion 144A constitutes a flow path to the corresponding outlet 141. Therefore, the air or water that has flowed into the divergence portion 144A flows into the corresponding outlet 141 by each recess, and is emitted through the corresponding outlet 141.

Further, a funnel-shaped or tapered diameter-reduced portion 143 is formed on the downstream side in the connecting pipe portion 142 and on the upstream side of the divergence portion 144A. The diameter of the connecting pipe portion 142 on the upstream side of the divergence portion 144A is reduced by the diameter-reduced portion 143. Therefore, the speed of air or water flowing into each divergence portion 144A through the diameter-reduced portion 143 becomes fast, and the injection force at the time of injection from each outlet 141 can be secured.

As described above, in the endoscope 10 according to the second embodiment of the invention, since the air supply/water supply nozzle 140 has five outlets 141 having different orientations, it is possible to prevent the separation from the curved surface of the observation optical system 132 in advance by air or water concentrating toward the center of the observation optical system 132, and it is possible to clean the observation optical system 132 up to the nozzle opposite side with air or water.

The same portions as those in the first embodiment are designated by the same reference numerals, and detailed description thereof will be omitted.

Third Embodiment

Figure 8:
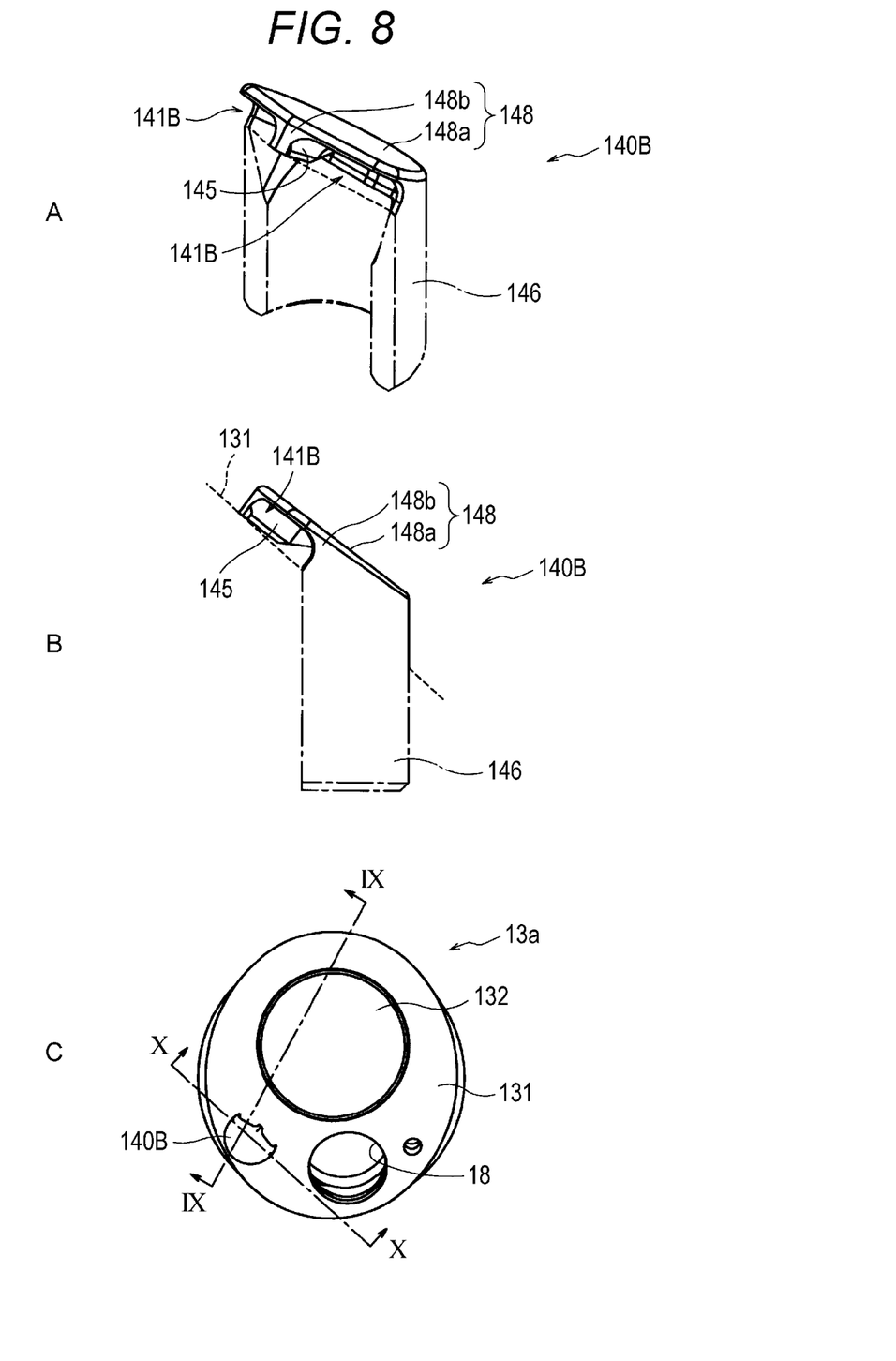
FIG. 8 is a diagram illustrating an air supply/water supply nozzle of an endoscope according to a third embodiment of the invention.

FIG. 8 is a diagram illustrating an air supply/water supply nozzle 140B of the endoscope 10 according to the third embodiment of the invention. FIG. 8A is a perspective view illustrating the appearance of the air supply water supply nozzle 140B, FIG. 8B is a side view of the air supply water supply nozzle 140B, and FIG. 8C illustrates a case where the air supply/water supply nozzle 140B is attached to the distal end portion 13*a*. In FIGS. 8A and 8B, the portion to be inserted into the recess provided on the distal end surface 131 is indicated by a chain line, and the distal end surface 131 is indicated by a broken line.

The air supply/water supply nozzle 140B of the endoscope 10 according to the third embodiment of the invention has a semi-cylindrical portion 146 inserted into a recess provided on the distal end surface 131, and one open end of the semi-cylindrical portion 146 is sealed by the lid portion 148. The lid portion 148 and the semi-cylindrical portion 146 are integrally formed.

The lid portion 148 has a peripheral wall 148*b* extending from the periphery of a substantially disc-shaped plate portion 148*a*. The peripheral wall 148*b* is provided with a predetermined dimension in the direction intersecting the plate portion 148*a*. The lid portion 148 is inclined with respect to the longitudinal direction of the semi-cylindrical portion 146. The area of the plate portion 148*a* is larger than the cross-sectional area in the radial direction of the semi-cylindrical portion 146, and a part of the lid portion 148 protrudes from the semi-cylindrical portion 146 in the radial direction of the semi-cylindrical portion 146.

Two outlets 141B are formed in the peripheral wall 148*b* relating to a part of the lid portion 148 with an interval therebetween. The outlet 141B has a semi-elliptical shape. In other words, the outlet 141B is formed in the part of the lid portion 148 by cutting out the peripheral wall 148*b* in a semi-circular shape. Therefore, the outlet 141B forms a hole together with the distal end surface 131. Air or water is injected into the observation optical system 132 through such a hole.

A fin-shaped guide portion 145 is projected from the inner surface of the plate portion 148*a*. The guide portion 145 guides air or water from a divergence portion 134, which will be described later, to the outlet 141B. The guide portion 145 is provided on the downstream side in the flow path of air or water from the divergence portion 134 to each outlet 141B, that is, closer to the outlet 141B. The guide portion 145 is provided in the vicinity of the two outlets 141B and between the two outlets 141B.

As described above, since the endoscope 10 according to the third embodiment of the invention includes the guide portion 145, the emission direction (injection direction) of air or water emitted from the outlet 141B can be accurately adjusted.

Unlike the first and second embodiments, in the third embodiment, the connecting pipe portion, the divergence portion, and the diameter-reduced portion are provided at the distal end portion 13. The details will be described below.

Figure 9:
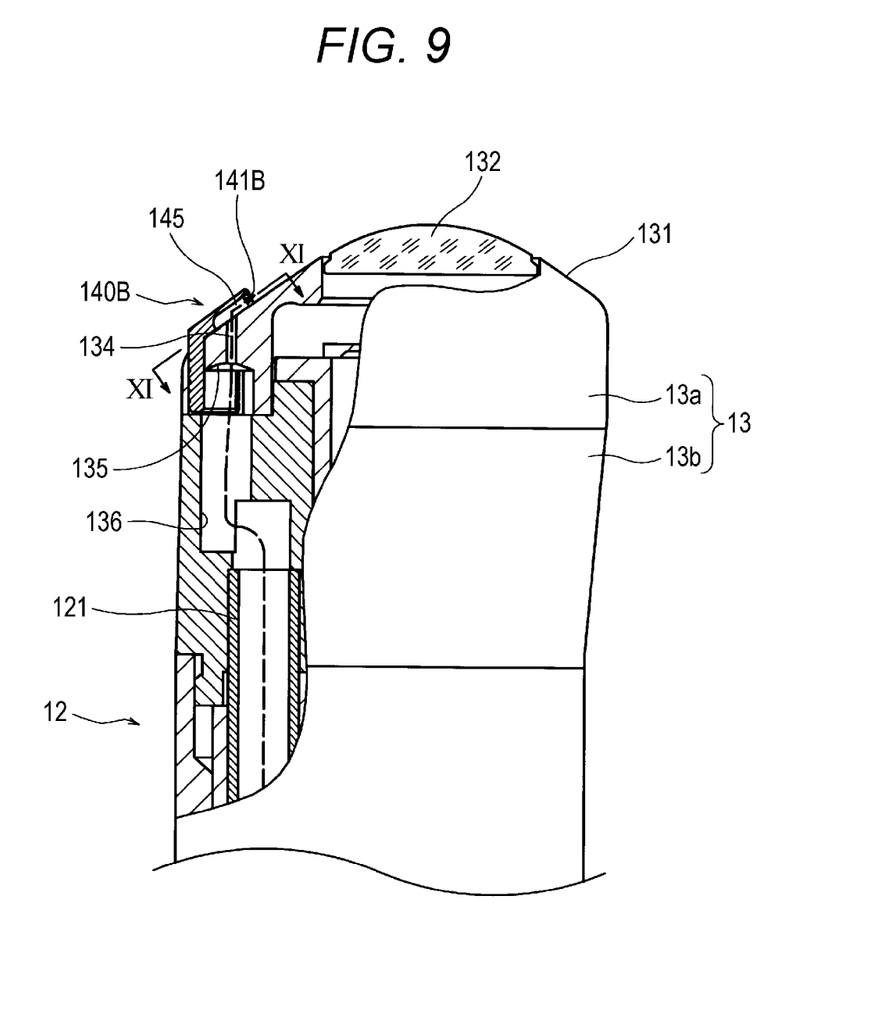
FIG. 9 is a cross-sectional view taken along line IX-IX in FIG. 8.
Figure 10:
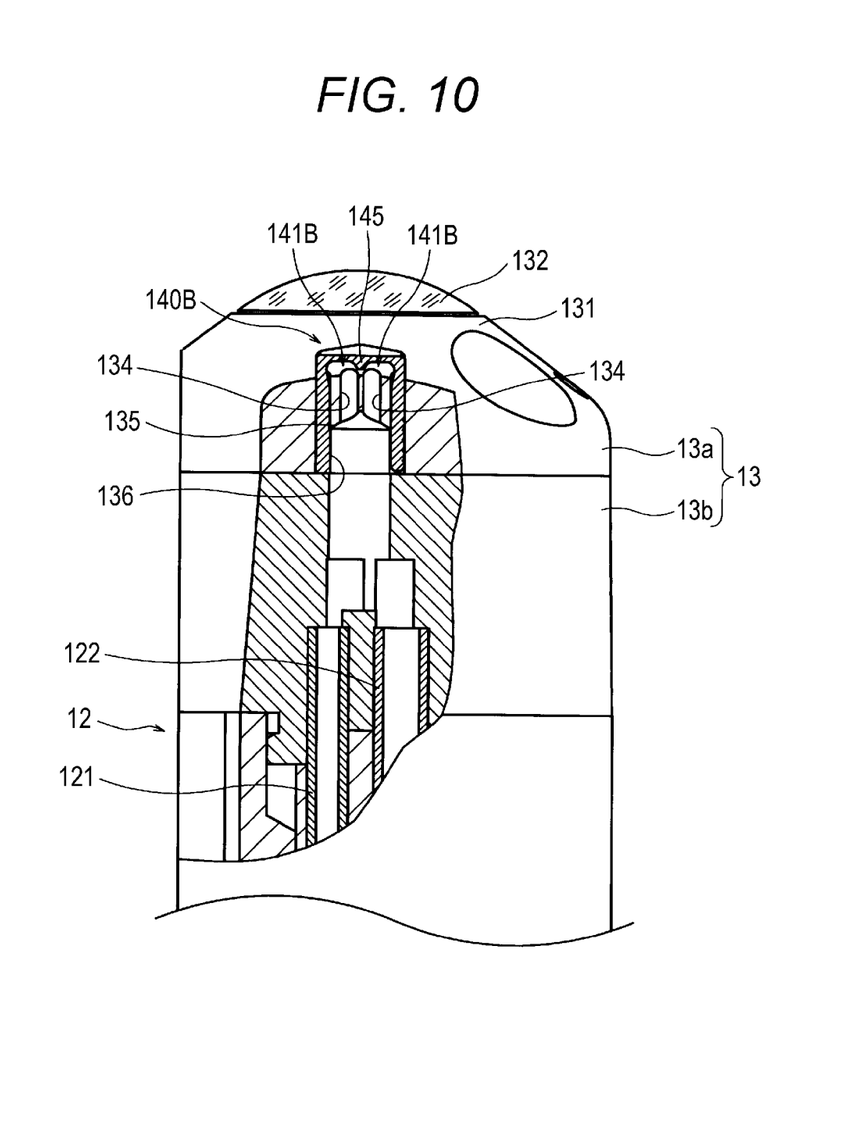
FIG. 10 is a cross-sectional view taken along line X-X of FIG. 8.
Figure 11:
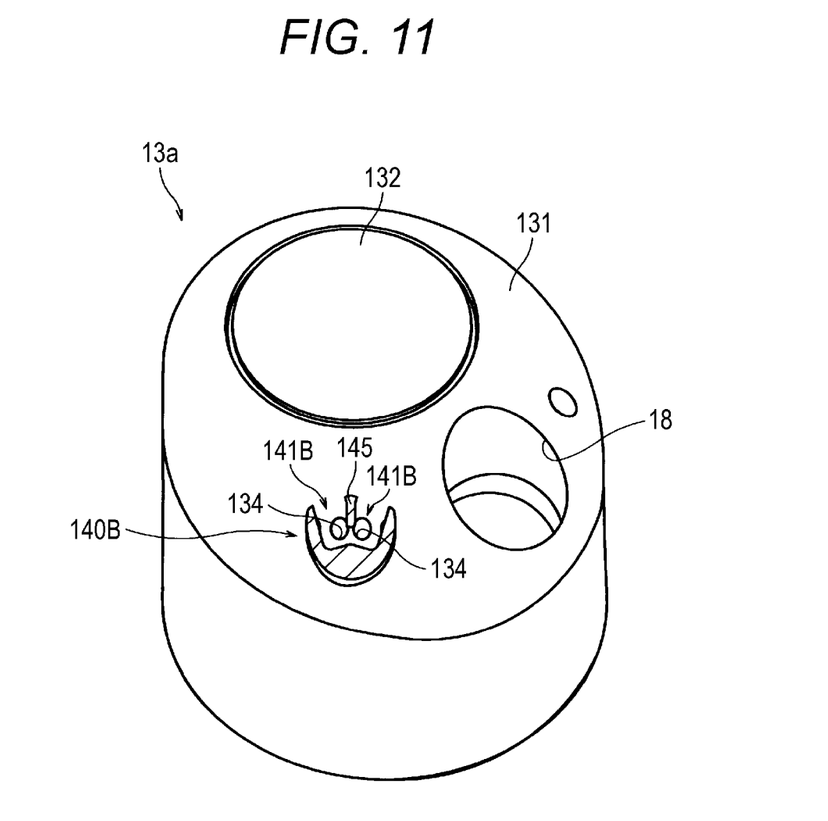
FIG. 11 is a cross-sectional view taken along line XI-XI of FIG. 9.

FIG. 9 is a cross-sectional view taken along line IX-IX of FIG. 8C, FIG. 10 is a cross-sectional view taken along line X-X of FIG. 8C, and FIG. 11 is a cross-sectional view taken along line XI-XI of FIG. 9.

Inside the distal end portion 13, a connecting pipe portion 136 extending along the longitudinal direction of the insertion portion 14 is provided. The connecting pipe portion 136 sends the air or water sent through the air supply tube 121 and the water supply tube 122 (fluid channel) to each outlet 141B. The air supply tube 121 (air supply channel) and the water supply tube 122 (water supply channel) penetrate the insertion portion 14 in the longitudinal direction, and are provided so as to straddle the bending section 12 and the distal end portion 13. The air supply tube 121 and the water supply tube 122 communicate with one end of the connecting pipe portion 136, and send the air or water from the folding portion 16 side to the connecting pipe portion 136. That is, the air or water that has flowed into the connecting pipe portion 136 via the air supply tube 121 and the water supply tube 122 is sent to the outlet 141B of the air supply/water supply nozzle 140B.

At the other end of the connecting pipe portion 136 on the downstream side, there is provided the divergence portion 134 that divides the flow of air or water flowing through the connecting pipe portion 136 corresponding to the number of outlets 141B. That is, the downstream side of the connecting pipe portion 136 is divided into two flow paths (the divergence portion 134) having a smaller diameter than the connecting pipe portion 136. The divergence portion 134 is open to the distal end surface 131 on both sides of the guide portion 145 (see FIG. 11). In this way, each divergence portion 134 is provided so as to correspond to any one of the outlets 141B. The air or water flowing out from each divergence portion 134 changes its direction by the plate portion 148a of the air supply/water supply nozzle 140B, and is emitted through the corresponding outlet 141B.

Further, a funnel-shaped or tapered diameter-reduced portion 135 is formed on the downstream side of the connecting pipe portion 136 and on the upstream side of the divergence portion 134. That is, the diameter of the connecting pipe portion 136 on the upstream side of the divergence portion 134 is reduced by the diameter-reduced portion 135. Therefore, the pressure of air or water flowing into each divergence portion 134 through the diameter-reduced portion 135 is reduced, and the flow speed is increased. The air or water having a higher flow speed flows out into a space wider than the divergence portion 134 (see FIGS. 9 and 10), and flows toward the outlet 141B. At this time, air or water forms a vortex having vectors in various directions, and is emitted from the outlet 141B. Therefore, the air or water injected from each outlet 141B spreads over a wide range, and can secure an injection force and range at the time of injection. FIG. 9 illustrates the flow path of air or water with a broken line.

In the endoscope 10 according to the third embodiment of the invention, the air or water sent to the connecting pipe portion 136 via the air supply tube 121 and the water supply tube 122 passes through the diameter-reduced portion 135 and the flow divergence portion 134 and is sent to the outlet 141B of the air supply/water supply nozzle 140B. As described above, the guide portion 145 is provided on the downstream side of the flow path of air or water from the divergence portion 134 to the outlet 141B, that is, near the outlet 141B. Therefore, the guide portion 145 guides the air or water to the outlet 141B. Air or water is emitted through the hole including the outlet 141B and the distal end surface 131.

As described above, in the endoscope 10 according to the third embodiment of the invention, the connecting pipe portion 136, the diameter-reduced portion 135, and the divergence portion 134 are provided inside the distal end portion 13, so that it is possible to provide the air supply/water supply nozzle 140B with a simple configuration.

The same portions as those in the first and second embodiments are designated by the same reference numerals, and detailed description thereof will be omitted.

The endoscope 10 according to the invention is not limited to the above description.

The size, shape, and the like of all the outlets 141 and 141B do not be necessarily the same.

Further, the plurality of outlets 141 and 141B may communicate with each other, but preferably does not communicate with each other.

It is desirable that the outlets 141 and the outlets 141B are spaced at a distance of 50% or less of their heights (dimensions in a direction perpendicular to the distal end surface 131).

In the above description, the case where the air supply tube 121 and the water supply tube 122 are connected to the connecting pipe portions 136 and 142, and the connecting pipe portions 136 and 142 are connected to the air supply/water supply nozzles 140 and 140B has been described. The endoscope 10 according to the invention, however, is not limited to the above description.

The air supply/water supply nozzles 140 and 140B for air supply directly connected to the air supply tube 121 and the air supply/water supply nozzles 140 and 140B for water supply directly connected to the water supply tube 122 may be provided, individually.

REFERENCE SIGNS LIST 10 endoscope
14 insertion portion
121 air supply tube (fluid channel)
122 water supply tube (fluid channel)
132 observation optical system
134, 144, 144A divergence portion
135, 143 diameter-reduced portion
136, 142 connecting pipe portion
140, 140B air supply/water supply nozzle
141, 141B outlet
145 guide portion

The invention claimed is:
1. An endoscope comprising:
an insertion portion extending in a longitudinal direction parallel to an insertion direction of the endoscope, the insertion portion having a distally-facing convex distal end and a proximal end on opposite ends of the insertion portion in the longitudinal direction;
a convex observation lens system provided on a distal-most end of the distally-facing convex distal end, wherein
a center of the observation lens system is eccentric to a center axis of the insertion portion in the longitudinal direction, and
a curvature of the observation lens system is continuous with a curvature of the distally-facing convex distal end; and
a nozzle for injecting a cleaning fluid toward the observation lens system and provided on the distally-facing convex distal end at a position proximal to the observation lens system,
wherein the nozzle includes a plurality of outlets from which the fluid is emitted in directions not intersecting with each other such that fluid is emitted from each outlet of the plurality of outlets in directions different from each other and toward a part of the observation lens system except a center of the observation lens system, and wherein the proximal end of the insertion portion is provided closer to an operation unit of the endoscope than the distally-facing convex distal end of the insertion portion.

2. The endoscope according to claim 1, comprising:
a connecting pipe portion for connecting a fluid channel passing through the insertion portion and the plurality of outlets; and
a divergence portion that is provided on a downstream side of the connecting pipe portion, and divides a flow of the fluid corresponding to the number of outlets.

3. The endoscope according to claim 2, comprising:
a guide portion provided on a downstream side of each flow path from the divergence portion to each outlet and guiding the fluid to each outlet.

4. The endoscope according to claim 2,
wherein the connecting pipe portion has a diameter-reduced portion on an upstream side of the divergence portion.

5. The endoscope according to claim 2,
wherein the fluid channel includes an air supply channel and a water supply channel, and
wherein the air supply channel and the water supply channel are connected to the connecting pipe portion.

6. The endoscope according to claim 1, wherein an entirety of the distal end of the insertion portion is a substantially conical shape.

7. The endoscope according to claim 1, wherein the nozzle is inclined toward the observation lens system with respect to the longitudinal direction.

\* \* \* \* \*